US008555889B2

(12) United States Patent
Mason et al.

(10) Patent No.: US 8,555,889 B2
(45) Date of Patent: Oct. 15, 2013

(54) POST-SURGICAL PROTECTIVE PILLOW

(76) Inventors: John E. Mason, Creve Coeur, MO (US); Bruce Thomas Vest, III, Godfrey, IL (US)

( * ) Notice: Subject to any disclaimer, the term of this patent is extended or adjusted under 35 U.S.C. 154(b) by 327 days.

(21) Appl. No.: 12/831,930

(22) Filed: Jul. 7, 2010

(65) Prior Publication Data
US 2012/0006333 A1    Jan. 12, 2012

(51) Int. Cl.
*A61G 15/00*    (2006.01)
(52) U.S. Cl.
USPC .......................................... 128/845; 128/846
(58) Field of Classification Search
USPC .............. 128/845, 846, 888; 5/643, 640, 636, 5/922, 652, 657, 630; 602/53; 297/452.21, 452.48
See application file for complete search history.

(56) References Cited

U.S. PATENT DOCUMENTS 5,347,668 A * 9/1994 Manning ........................... 5/622
6,151,734 A * 11/2000 Lawrie .............................. 5/640

* cited by examiner

*Primary Examiner* — Victoria J Hicks
(74) *Attorney, Agent, or Firm* — Don W. Weber

(57) ABSTRACT

A protective pillow for post-surgical use has a pliable yet firm inner incision pad and a stiff outer board. The outer board has handles on one side and is attached on the other side to the incision pad by use of hook-and-pile fasteners. The incision pad is soft yet pliable. The pad has one side with a cushioned surface. The cushioned surface has a long groove cut out from the inner part of the pad. The other side of the pad is attached to the outer board by hook-and-pile fasteners. The fasteners allow the post-surgical patient to orient the incision groove in any direction desirable so as to align the groove with the actual incision. The handles on the outer board always remain essentially horizontal while the incision pad is oriented in the same direction as the incision. The pad and board may be removed for easy cleaning or replacement.

3 Claims, 5 Drawing Sheets

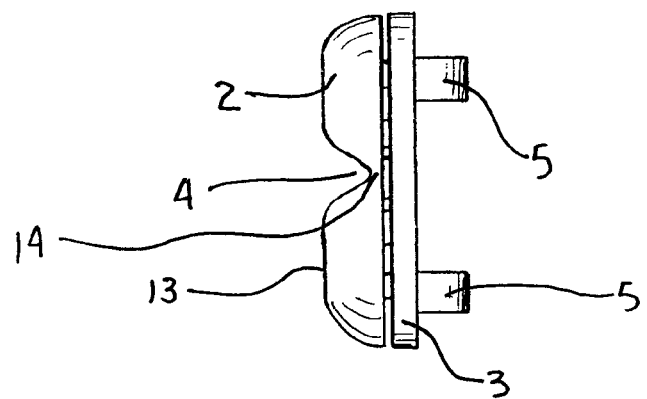
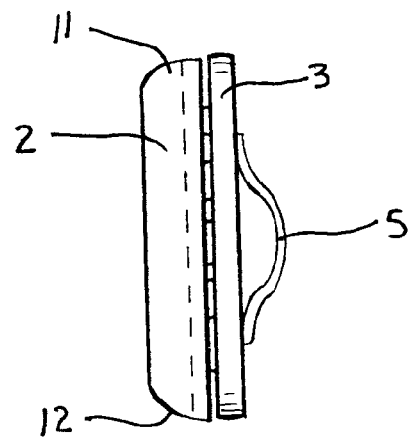
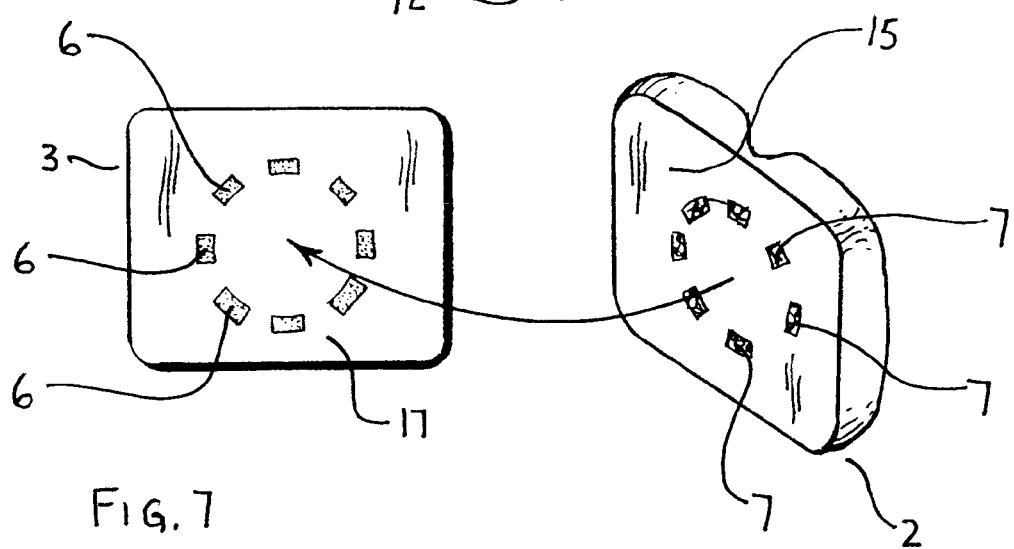

POST-SURGICAL PROTECTIVE PILLOW

BACKGROUND OF THE INVENTION

This invention relates to the field of post-operative devices. In particular, a post-operative surgical pillow is presented that allows the patient to orient the pad in the same direction as the actual surgical incision.

After surgery, an incision is sewn or otherwise reattached and left to heal. The incision is generally elongated and may be of varying lengths, the most common incision length being approximately six inches. Normally the area directly next to the incision is painful, especially when a patient has any physical exertion. When a patient coughs or sneezes, the wound may break open causing harmful effects and possibly necessitating another trip to the surgeon or emergency room. In addition, simply moving, getting up out of bed or from a chair may cause a stress on the incision. It is an object of this invention to provide a protective pillow to encourage coughing and enabling the patient to get up from the lying position without experiencing any pain related to such physical activity.

Several devices currently on the market address the problem of post-operative motion and surgical incisions. For example, the 1989 patent issued to Yon (U.S. Pat. No. 4,829,613) for a protective pad for post-operative recovery disclosed a heart-shaped pad that could be pressed close to the patient for supporting the sternum when the patient coughs. While useful in certain conditions, the Yon pad did not make allowance for supporting the area around the incision while not pressing against the actual incision. It is an object of this invention to provide a pad for supporting the area around an incision while not touching the actual incision site.

Another approach to this problem was disclosed in the 1987 US patent issued to Lagin (U.S. Pat. No. 4,683,601). Lagin described a medical pillow which encircled part of the post-surgical torso. Many incisions are in fact horizontal or vertical and Lagin could be useful in those instances. However, Lagin did not provide support for the different orientations of surgical incisions. It is another object of this invention to provide support for the areas around surgical incisions, whether or not the incision is vertical, horizontal or other orientation.

A post-surgical sling was disclosed in the 1992 patent issued to Box, U.S. Pat. No. 5,154,691. The Box pillow was attached to the patient by straps and would remain at the set compression once fitted to the patient's body. It is a still further object of this invention to provide a post-surgical protective pillow that can be used intermittently and at varying degrees of compression to cushion and support the area around a surgical wound.

Other and further objects of this invention will become obvious upon reading the Specification below.

BRIEF DESCRIPTION OF THE INVENTION

The instant invention is a post-surgical pillow used to cover the surgical incision made during an operation. The device comprised two sections, an outer essentially rectangular board having outer handles and a matching inner softer incision pad. The incision pad has an elongated surgical incision groove formed near the center of the pad. The incision pad and the board may be attached by Velcro® hook and pile fasteners such that the incision groove may be oriented in any direction with respect to the actual incision. The patient places the groove along the length of a surgical incision and holds the device next to his body while moving, eating coughing, sneezing or other physical activity to help maintain the integrity of the incision as it heals.

BRIEF DESCRIPTION OF THE DRAWING FIGURES

FIG. 5 is a top view of the device.

FIG. 6 is a side view of the device.

FIG. 7 is an exploded view of the device showing the adjacent surfaces between the board and the incision pad.

DETAILED DESCRIPTION OF THE INVENTION

Figure 1:
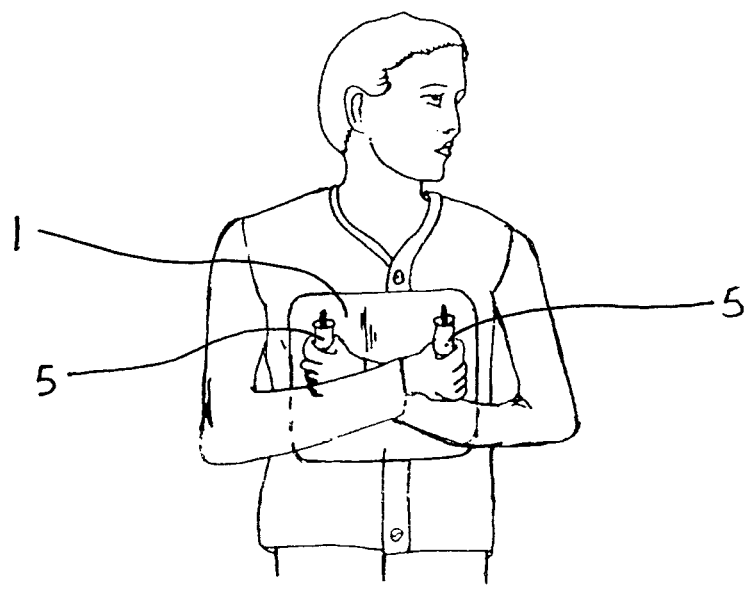
FIG. 1 is a perspective view of the device as it is used with a post-surgical patient.
Figure 2:
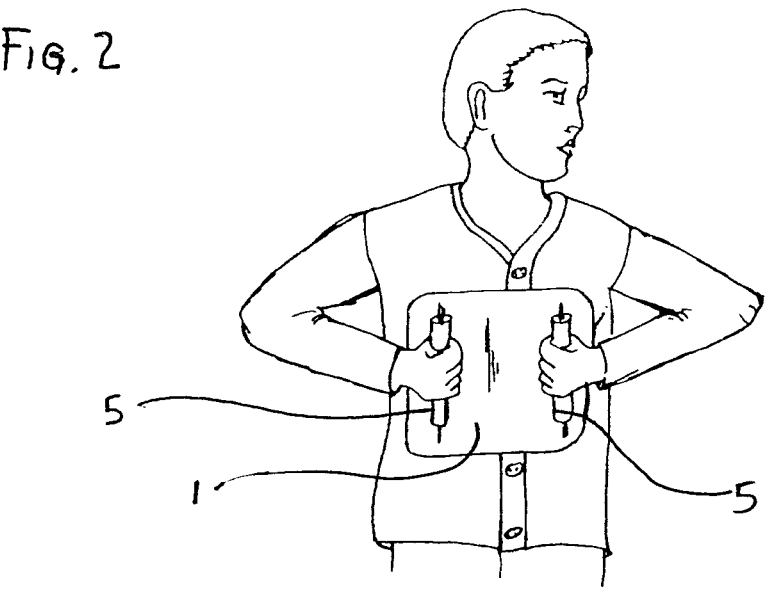
FIG. 2 is a perspective view of the device showing an alternate method of using the pillow.

A post-surgical protective pillow 1 is shown in FIGS. 1 and 2. The pillow is designed to protect the patient as he walks, moves, coughs, sneezes or in other situations where it is imperative that the incision not absorb the strain of the physical movement or activity. The pillow has handles 5 shown on FIGS. 1 and 2 so that it may be held against the incision. The post-surgical patient may hold the pillow 1 against his body as shown with such pressure as he deems appropriate and comfortable.

Figure 3:
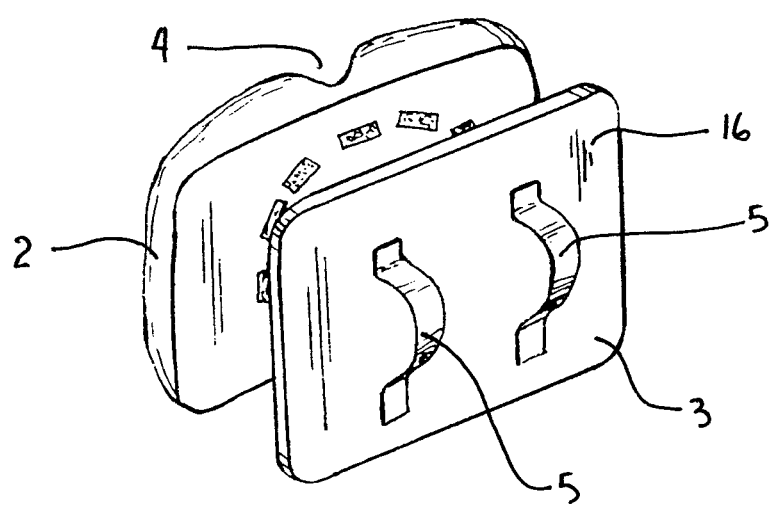
FIG. 3 is a perspective exploded view of the device showing soft handles.

Turning to FIG. 3, the pillow is shown comprising two main parts, a pliable incision pad 2 and a harder outer board 3. The incision pad 2 may be made of any type of suitable material that is both soft enough for comfort yet firm enough to keep its shape when held against the body of the patient. Memory foam, sports type EVA foam or similar materials are suitable for the pad part 2 of the device. The preferred embodiment of the pad part 2 of the device is essentially rectangular as shown with dimensions of approximately thirteen inches long and ten inches in height. The pad 2 would be approximately three to four inches wide. Obviously, these dimensions are for information only and are not meant as a limitation. Further, the pad 2 may have straight top 11 and bottom 12 edges or the pad may be slightly curved to simulate the curve of the patient's body.

Figure 11:
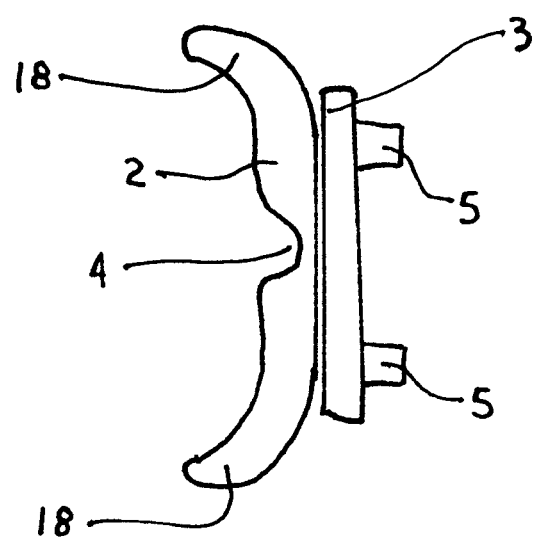
FIG. 11 is a top view of an alternate embodiment of the device similar to FIG. 5 showing a curved incision pad.

Different sizes and geometric shapes of the device are well within the spirit of this disclosure. For example, the incision pad may have a curved incision side surface as best shown in FIG. 11. This curved surface has wings 18 curved toward the body of the patient.

An important feature of the incision pad 2 is the elongated incision groove 4. The elongated incision groove 4 is formed near the center of the incision side 13 of the pad 2. This elongated groove 4 is indented approximately three-fourths of the width of the pad 2 such that it forms an incision groove and yet has some padding 14 between the depth of the groove and the attaching side 15 of pad 2. In use, the incision groove 4 is placed along the patient's incision while the remaining part of pad 2 is used as a cushion or pillow to protect the wound area.

A stiff outer board 3 is used to keep the device in place along the incision. The outer board may be made of lightweight plastic or other suitable lightweight yet strong material. The outer board 3 and the pad 2 have matching shapes in the preferred embodiment shown in FIGS. 1 through 10 such that they have the same perimeter and outline when attached to each other as best shown in FIGS. 5 and 6. The outer board 3 has a handle side 16 and an attaching side 17 as shown on FIG. 7.

Figure 4:
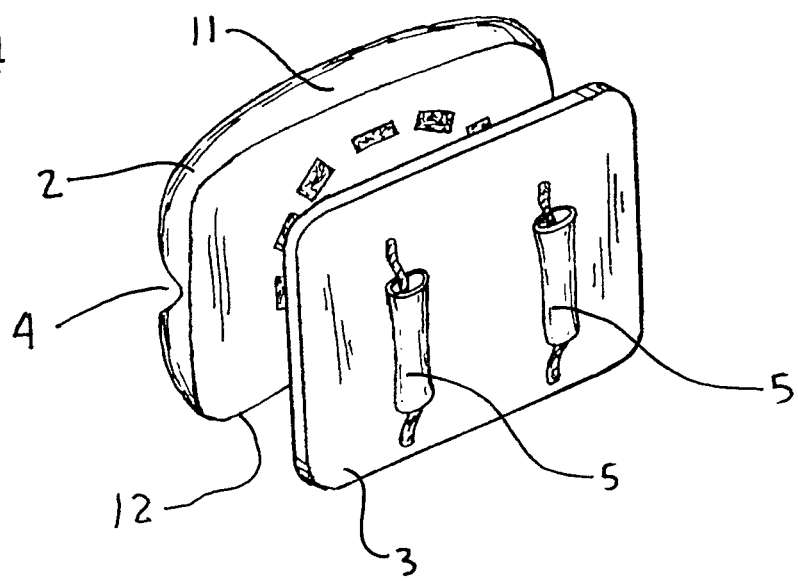
FIG. 4 is a perspective exploded view of the device showing an alternate embodiment of the handles.

In the preferred embodiment, a pair of handles 5 is attached to the handle side 16 of outer board 3 as best shown in FIGS. 3 through 6. These handles 5 are approximately one and one-half inches in length and are essentially parallel to each other. The handles are attached such that the patient may easily grasp them for holding the device next to the wound as shown in FIGS. 1 and 2. For a two-handle device, each handle is approximately two inches from a vertical edge of the board 3. While two handles are preferred, this is described here as an illustration only and is not meant as a limitation on the scope of the invention. While it has been found that two handles are preferred, one handle or multiple handles could also be used in practicing this invention. The handles 5 may be made of soft yet strong cloth type material as shown in FIG. 3 or may be cord handles with covers as shown in FIG. 4.

Figure 8:
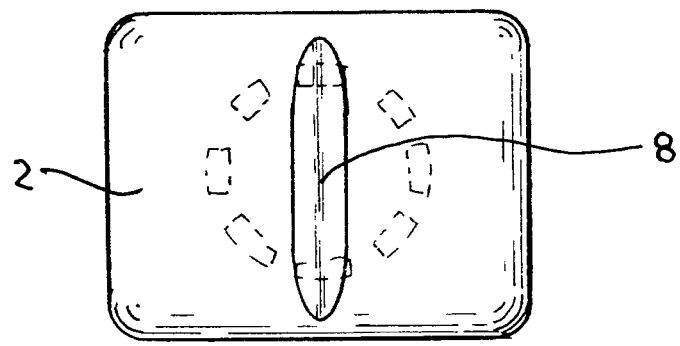
FIG. 8 is a view of the device showing the incision side of the device with the incision groove in the vertical orientation.
Figure 9:
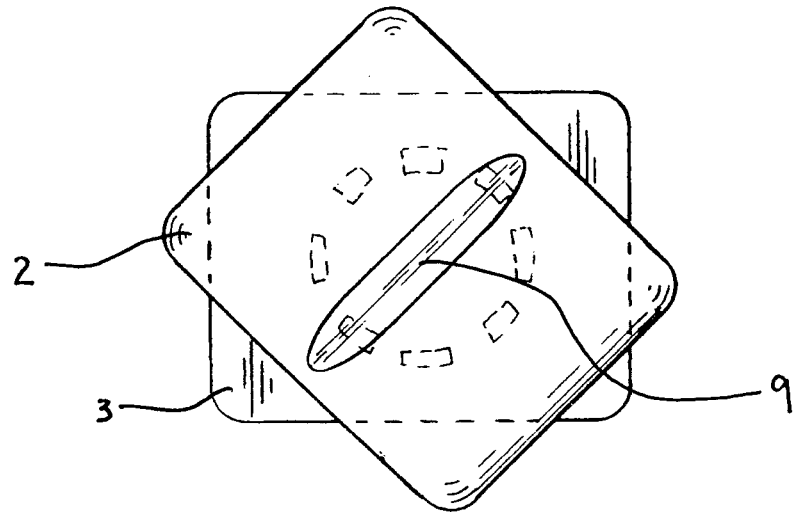
FIG. 9 is a view of the device showing the incision side of the device with the incision groove in the forty-five degree orientation.
Figure 10:
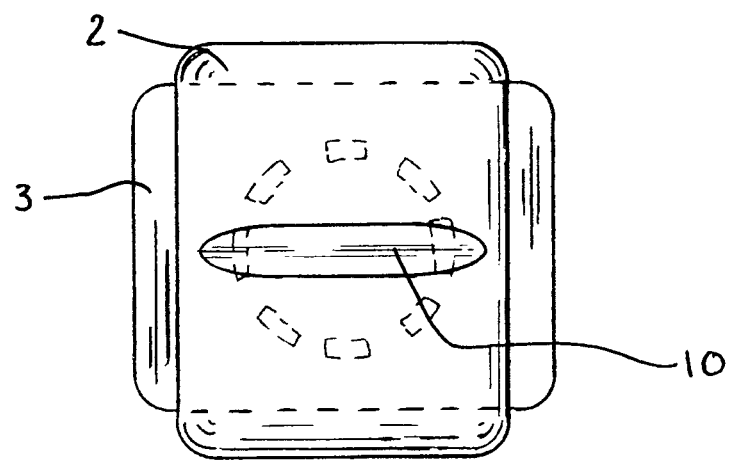
FIG. 10 is a view of the device showing the incision side of the device with the incision groove in the horizontal orientation.

The attaching side 15 of pad 2 and the attaching side 17 of board 3 have corresponding hook 6 and pile 7 fasteners, respectively. In the preferred embodiment shown in FIG. 7, corresponding hook 6 and pile 7 fasteners are secured to the respective surfaces 17 and 15. However other types of fasteners such as buttons and snaps could also be used. This hook-and-pile fastening system allows the patient to orient the direction of the incision groove 4 in any convenient and applicable manner so as to align the incision groove 4 with the actual incision on the patient. For example, if the incision made during surgery was a vertical one, the incision groove orientation 8 would be as shown in FIG. 8. If the incision made was at a forty-five degree angle, the incision groove orientation 9 would be as shown in FIG. 9. If the incision were horizontal across the torso, the incision groove orientation 10 would be as shown in FIG. 10. This particular adjustable feature of the device is an important improvement in this field since it allows the patient to hold the board part of the protective pillow in the same orientation to the torso (i.e. across the torso in the horizontal position) regardless of the orientation of the actual incision. This feature allows the handles to be utilized in an easy, simple and efficient manner while covering the incision as required.

In order to effectively use the device when necessary, one first aligns the incision grove 4 with the actual incision made by the surgeon. Having once aligned the groove properly, the protective pillow may than be placed over the incision when required, as shown in FIGS. 1 and 2 for moving, coughing, sneezing or for other reasons. Since the handles are always horizontal to each other as shown in FIGS. 1 and 2, it is much easier for the patient to align the groove to the incision properly without viewing the groove itself. The pad 2 protects and supports the area around the incision while not contacting the actual incision site itself.

Since the pad and the outer board are two separate pieces, they may be removed for easy cleaning or the pad, which is in contact near the wound, may be replaced.

Having fully described my device, We claim:

1. A protective pillow for covering and supporting an area around a surgical incision in a body of a patient, comprising:
    (a) a stiff outer board having a handle side and an attaching side, wherein said handle side has at least one handle, wherein said at least one handle is made of soft yet strong cloth material or comprises cord handles with covers, and wherein said at least one handle is adapted to be grasped for the patient to hold the protective pillow next to the surgical incision;
    (b) a pliable incision pad having an incision side and an attaching side, wherein said incision side has an elongate incision groove therein, and wherein the pliable incision pad is firm enough to keep its shape when held against the body of the patient,
    wherein said elongate incision groove is formed near the center of the pliable incision pad and is adapted to be placed along a length of the surgical incision
    and wherein there is some padding between a depth of the elongate incision groove and the attaching side of said pliable incision pad
    and wherein said pliable incision pad is adapted to protect and support the area around said surgical incision while said pliable incision pad does not contact the surgical incision itself,
    and wherein said pliable incision pad has straight top and bottom edges, and said pliable incision pad and stiff outer board are essentially rectangular,
    and wherein said pliable incision pad has a shape matching that of said stiff outer board with a same perimeter and outline when attached to each other;
    wherein said stiff outer board and said pliable incision pad are removeable attached together at their attaching sides such that an orientation of said elongate incision groove is adapted to be adjusted to align the elongate incision groove with the surgical incision in the body of the patient.

2. The protective pillow for covering and supporting the area around a surgical incision as in claim 1, wherein the attaching sides of said stiff outer board and pliable incision pad have corresponding hook-and-pile surfaces.

3. The protective pillow for covering and supporting the area around a surgical incision as in claim 1, wherein the attaching sides of said stiff outer board and pliable incision pad have corresponding fasteners.

* * * * *